US011000495B2

(12) United States Patent
Johnson et al.

(10) Patent No.: US 11,000,495 B2
(45) Date of Patent: May 11, 2021

(54) TOPICAL DICLOFENAC SODIUM COMPOSITIONS

(71) Applicant: Novartis Consumer Health S.A., Nyon (CH)

(72) Inventors: Gregory Johnson, Lincoln, NE (US); Eric Woodward, Lincoln, NE (US)

(73) Assignee: GSK Consumer Healthcare S.A., Prangins (CH)

( * ) Notice: Subject to any disclaimer, the term of this patent is extended or adjusted under 35 U.S.C. 154(b) by 0 days.

(21) Appl. No.: 15/506,774

(22) PCT Filed: Sep. 9, 2015

(86) PCT No.: PCT/IB2015/056907
§ 371 (c)(1),
(2) Date: Feb. 27, 2017

(87) PCT Pub. No.: WO2016/038553
PCT Pub. Date: Mar. 17, 2016

(65) Prior Publication Data
US 2017/0281580 A1    Oct. 5, 2017

Related U.S. Application Data

(60) Provisional application No. 62/048,629, filed on Sep. 10, 2014.

(51) Int. Cl.
| | | |
|---|---|---|
| *A61K 31/196* | (2006.01) | |
| *A61K 9/00* | (2006.01) | |
| *A61K 47/10* | (2017.01) | |
| *A61K 47/00* | (2006.01) | |
| *A61K 9/107* | (2006.01) | |
| *A61K 9/06* | (2006.01) | |

(52) U.S. Cl.
CPC .......... *A61K 31/196* (2013.01); *A61K 9/0014* (2013.01); *A61K 9/06* (2013.01); *A61K 9/107* (2013.01); *A61K 47/00* (2013.01); *A61K 47/10* (2013.01)

(58) Field of Classification Search
CPC ...... A61K 31/196; A61K 47/10; A61K 47/00; A61K 9/0014; A61K 9/107; A61K 9/06
See application file for complete search history.

(56) References Cited

U.S. PATENT DOCUMENTS

| | | | |
|---|---|---|---|
| 4,407,824 | A | 10/1983 | Eckert |
| 4,670,254 | A | 6/1987 | Kamishita |
| 4,917,886 | A | 4/1990 | Asche et al. |
| 5,350,769 | A | 9/1994 | Kasai et al. |
| 7,732,489 | B2 | 6/2010 | Steiger |
| 8,557,870 | B2 | 10/2013 | Steiger |
| 8,716,340 | B2 | 5/2014 | Steiger |

| | | | |
|---|---|---|---|
| 2004/0101538 | A1 | 5/2004 | Larnier et al. |
| 2010/0286268 | A1 | 11/2010 | Caillett-Bois et al. |
| 2011/0237674 | A1* | 9/2011 | Zhang .................. A61K 9/0014 514/567 |

FOREIGN PATENT DOCUMENTS

| | | |
|---|---|---|
| CZ | 290752 B6 | 10/2002 |
| DE | 33 36 047 A1 | 4/1984 |
| EP | 1457202 A2 | 9/2004 |
| EP | 2214642 B1 | 10/2008 |
| JP | H 0912452 A1 | 1/1997 |
| WO | WO 93/00873 A1 | 1/1993 |
| WO | WO 97/42944 | 11/1997 |
| WO | WO 97/42944 A1 | 11/1997 |
| WO | WO 00/51575 A1 | 9/2000 |
| WO | WO 02/11700 A1 | 2/2002 |
| WO | WO 02/17905 A2 | 3/2002 |
| WO | WO 02/078648 A2 | 10/2002 |
| WO | WO 2004/017998 A2 | 3/2004 |
| WO | WO 2004/030665 A1 | 4/2004 |
| WO | WO 2005/025571 | 3/2005 |
| WO | WO 2007/065281 | 6/2007 |
| WO | WO 2009/063493 | 5/2009 |
| WO | WO 2010/045415 A2 | 4/2010 |

OTHER PUBLICATIONS

Voltaren Gel Label, Sep. 23, 2009.
Voltarol 2.3% Emulgel; 2013.
Voltarol® 1.16% Emulgel® Gel Patient Information Leaflet.
Solaraze® Product Label; Dec. 2011.
Pennsaid® Prescribing Information (diclosfenac sodium topical solution); Jan. 2014.
Panwar et al., Emulgel: A Review; Asian Journal of Pharmacy and Life Science; vol. 1(3), Jul.-Sep. 2011, 333-343.
JPH0912452A1 Translation of D19 into English; Drug Dev. Ind. Pharm. 2000, 26(4), 375-381.
Agnihotri, S.A. et al., "Electrically Modulated Transport of Diclofenac Salts Through Hydrogels of Sodium Alginate, Carbopol, and their Blend Polymers," J. Appl. Polym. Sci., 96 (2), 301-311 (2005).
Caraballo, I., "Expert Opinion," Nov. 20, 2019.
Datapharm Communications, Medicines Compendium 2005, Datapharm Communications Ltd, 2005, 2201-2202.
Fang, J-Y et al., "Influence of Electrical and Chemical Factors on Transdermal Iontophoretic Delivery of Three Diclofenac Salts," Biol. Pharm. Bull., 2001, 24(4), 390-394.

(Continued)

*Primary Examiner* — Sarah Pihonak
*Assistant Examiner* — Jason Deck
(74) *Attorney, Agent, or Firm* — Diane E. Furman

(57) ABSTRACT

The invention relates to beneficial topical pharmaceutical compositions comprising diclofenac sodium in high amounts, and methods for their use. Said compositions represent emulsion-gels as well as gels with unique properties such as high skin penetration, no irritation, high stability, complete dissolution of the active and effective pain relief. The invention also provides methods for treating pain or inflammation in a mammalian subject in need thereof, including acute and chronic pain or inflammation; and kits therefor.

31 Claims, 5 Drawing Sheets

(56) References Cited

OTHER PUBLICATIONS

Fini, A. et al., "Formation of ion-pairs in aqueous solutions of diclofenac salts," Int. J. Pharm., 187, 163-173 (1999).

Florence, A.T. and D. Atwood, Physicochemical Principles of Pharmacy, 3rd Edition, Palgrave, Hampshire (1998), 264-66 and 319-20.

Fox, C., "Skincare: An Overview and Update on the State of the Art and Science," Cosmetics and Toiletries, 1984, 99, 41-54.

Hitti, M., "FDA Oks Voltaren Gel for Osteoarthritis," WebMD Health News, Oct. 23, 2007.

Khalil, E. et al., "Aqueous Solubility of Diclofenac Diethylamine in the Presence of Pharmaceutical Additives: A Comparative Study with Diclofenac Sodium," Drug Dev. Ind. Pharm., 26 (4), 375-381 (2000).

Kriwat, K. and C.C. Muller-Goymann, "Binary Diclofenac Diethylamine Water systems: Micelles, Vesicles and Lyotropic Liquid Crystals," Eur. J. Pharm. Biopharm., 39, 234-238 (1993).

Minghetti P. et al., "Ex Vivo Study of Transdermal Permeation of Four Diclofenac Salts from Different Vehicles," J. Pharma. Sci, 2007, 96(4), 814-823.

PharmaCircle—Molecule—Diclofenac diethylamine (Jan. 23, 2019).

Shalaby, S. and N.S. Bassily, Evaluation of in-vitro permeation and anti-inflammatory effect of diclofenac and its salts a histological analysis, Saudi Pharm. J., 10 (1), 19-29 (2002).

Smith, E.W. and H.I. Maibach, ed., Percutaneous Penetration Enhancers, CRC Taylor and Francis Group, 2006, Ed. 2, Chapter 12, 137-138,153-154.

Trommer, H. and R.H.H. Neubert, "Overcoming the Stratum Corneum: The Modulation of Skin Penetration," Skin Pharmacol. Physiol. 2006, 19,106-121.

Van Boxtel, C.J. et al., Drug Benefits and Risks, International Textbook of Clinical Pharmacology, John Wiley & Sons, 2001, 577.

Paper filed in App No. 12740041 (Mar. 13, 2015) cited in Opposition.

Paper filed in App No. 12740041 (Sep. 8, 2015) cited in Opposition.

EPO Communication and Ref. D5 (English translation of CZ290752) (Feb. 13, 2018).

Interlocutory Decision of EPO Opposition Division, 2 214 624 (Aug. 1, 2019).

Letter and Exhibits D9c, EPO Opposition, 2 214 642 (Jun. 19, 2018).

Minutes of Oral Proceedings, EPO Opposition, 2 214 642 (Dec. 3, 2020).

NDA Approval Letter, VOLTAREN Gel (Oct. 17, 2007) with product formulation sheet (Feb. 28, 2020).

\* cited by examiner

TOPICAL DICLOFENAC SODIUM COMPOSITIONS

This application is a 371 of International Application No. PCT/IB2015/056907, filed Sep. 9, 2015, which claims the benefit of 62/048,629 filed Sep. 10, 2014.

BACKGROUND OF THE INVENTION

Topical, transdermal products comprising diclofenac, a non-steroidal anti-inflammatory drug (NSAID) of the acetic acid class, or a pharmaceutically acceptable salt thereof, are currently available to patients and consumers in the U.S. and other countries, and are widely used for their analgesic and anti-inflammatory properties, at reduced risk of the systemic adverse effects that can be experienced with oral NSAID formulations.

Acidic diclofenac has very low water solubility since the only hydrophilic functional group, i.e., the carboxyl group, is involved in the formation of a dimer and therefore not readily available to interact with solvent (Fini et al., "Diclofenac Salts, VIII. Effect of the Counterions on the Permeation through Porcine Membrane from Aqueous Saturated Solutions," *Pharmaceutics* 2012, 4, 413-429). Salt forms are often preferred in commercial topical formulations to address solubility problems with the acid; however, the solubility of the sodium salt of diclofenac is still quite low, its kinetic solubility being reported as 40±5 μg/mL for the anhydrous form (Llinas et al., "Diclofenac Solubility: Independent Determination of the Intrinsic Solubility of Three Crystal Forms," J Med Chem. 2007 Mar. 8; 50(5):979-83).

A low, i.e. 1%, concentration diclofenac sodium topical, transdermal product, formulated as an emulsion-gel ("emulgel"), was approved by the Food and Drug Administration (FDA) in 2007 as being safe and effective for the relief of the pain of osteoarthritis of joints amenable to topical treatment, such as the knees and those of the hands, when topically dministered in a four times-daily regimen to lower and/or upper extremities, and is marketed in the U.S. as Voltaren® Gel (diclofenac sodium emulgel, 1%; referred to herein as "DSG 1%" unless otherwise indicated). Studies show that systemic exposure with the recommended use of DSG 1% (4×4 g per day applied to 1 knee) is on average 17 times lower than with oral treatment given as 3×50 mg per day; and the average peak plasma concentration is 158 times lower than with the oral treatment.

Additionally, a 1.16% diclofenac diethylammonium (DEA) (equivalent to 1% sodium) topical emulgel was first approved in Europe in 1985 as Voltaren® (or Voltarol®) 1.16% Emulgel®, and is currently marketed in over 115 countries; see also GB 2,128,087. The DEA formulation has been approved for, e.g., relief of pain, inflammation, and swelling in post-traumatic inflammation of tendons, ligaments, muscles and joints (e.g., due to sprains, strains or bruises), localized forms of soft-tissue rheumatism (e.g., tendonitis, epicondylitis, shoulder-hand syndrome and peri-arthropathy), and the local management of degenerative joint conditions (e.g., osteoarthritis of the peripheral joints and of the vertebral column). A 2.32% strength diclofenac DEA (equivalent to 2% sodium) emulgel, containing oleyl alcohol as a permeation enhancer, has also been introduced under the Voltaren® (Voltarol®) name (and is hereinafter referred to as "VEG 2%"), affording to patients and consumers outside the U.S. the convenience of a twice-daily (b.i.d.) dosing regimen; see WO 2009/056522. However, the DEA salt form of diclofenac is not an approved salt form in the U.S.

Other topical, transdermal diclofenac sodium products include Solaraze®, a 3% gel for the treatment of actinic keratoses which relies on hyaluronate sodium as a penetration enhancer; as well as Pennsaid® 1.5% and 2% solutions comprising dimethylsulfoxide (DMSO) as a penetration enhancer.

It has been a key objective of the inventors to provide to patients and consumers in the U.S. as well as other markets a higher strength, i.e. up to about 5%, diclofenac sodium topical, transdermal product that may be applied less frequently but with similar or even superior effectiveness to DSG 1%. A reduced dosing schedule would provide an important benefit in facilitating patient compliance in proper usage of the product.

A specific objective has been to provide a higher strength topical, transdermal, diclofenac sodium composition in the form of an emulgel or a gel. As would be understood by the worker in the art, by "emulgel" is meant a dosage form comprising both an emulsion (e.g., oil-in-water or water-in-oil) and a gel (e.g., a hydrogel or hydroalcoholic gel), see, e.g., Panwar et al., "Emulgel: A Review," *Asian Journal of Pharmacy and Life Science*, Vol. 1 (3), July-September, 2011, 333-343. Emulgels, in particular, possess the advantages of both emulsions and gels and typically find high patient acceptability due to the properties of being thixotropic, greaseless, easily spreadable, easily removable, emollient, etc.

It has also been an important objective to provide a 1% or greater strength pharmaceutically acceptable diclofenac sodium composition which facilitates high, constant and reproducible permeation of the active. Therapeutic efficacy of a higher strength product requires that the higher amount of diclofenac in the composition be absorbed by the skin and penetrate in sufficient quantities into the targeted inflamed tissues or synovial fluid of the joints. A composition of 2% diclofenac sodium, for example, would preferably facilitate skin permeation of the active at a rate which is at least twice that of DSG 1%.

The skin, however, is a natural barrier, its external layer, the stratum corneum, acting as a hydrophobic barrier to percutaneous absorption of most drugs, especially hydrophilic or ionized ones such as diclofenac sodium. Achieving the desired permeation profile of diclofenac from a higher (i.e. >1%) concentration formulation could be expected to require the assistance of additional permeation enhancers, such as the oleyl alcohol in VEG 2%, DMSO or hyaluronic acid or salts thereof, or the like.

It has been another objective to provide a composition having very low systemic absorption, preferably as demonstrated by an AUC value (area under curve from t=0 to T=12 h) of less than 30 μg× hour/mL.

Yet another objective has been to provide a composition that is essentially non-irritating to human skin upon administration. The local skin tolerance of DSG 1% as well as VEG 2% is known to be very good in both cases, i.e. the appearance of skin irritations after application is rare, and also the systemic toxicity of said product is very low. Thus an objective of the present invention is to meet or exceed the safety profile set by these products.

A still further objective has been to achieve stable compositions suitable for commercial marketing in being resistant to phase separation and maintaining gel elasticity upon administration to the skin.

Finally, it has been an objective to prepare an emulgel or gel composition having similar aesthetics (i.e. skin feel, quick drying, cooling sensation) as those associated with the marketed products.

However, in attempting to meet the above objectives, the inventors had to confront several technical challenges: First, the low water solubility of the sodium salt at concentrations rising above 1% can result in crystal formation that raises a substantial risk of non-uniform dosing. Second, the sodium salt in higher concentrations can offset the gelling efficacy of the gel-forming component of the composition (e.g., carbomer), thereby reducing viscosity below an acceptable range. The inventors initially found, for example, that simply doubling diclofenac sodium concentration in the same formulation vehicle as used for DSG 1% is not technically feasible. Third, is the essential unpredictability whether a composition, even if meeting the first two challenges, will facilitate sufficiently high permeability and flux of the active to be therapeutically effective, let alone permit a reduced (e.g., twice-, or thrice-daily) dosing regimen. Thus, the inventors were faced with the overall challenge of striking an elusive balance between solubilizing the active, maintaining sufficient viscosity of the composition, and achieving high permeation and flux.

SUMMARY OF THE INVENTION

In experimenting with ternary solvent systems comprising water, a volatile water-miscible organic solvent and a non-volatile water-miscible organic solvent, the inventors have identified solvent systems in specific proportions that are effective to solubilize diclofenac sodium at concentrations of 1% or greater, and thus are found suitable to be utilized in the preparation of novel, stable emulgel and gel compositions of the invention.

Furthermore, such ternary solvent systems, when utilized in the preparation of an emulgel or gel, are found to provide pharmaceutical compositions of the invention that facilitate permeability of diclofenac sodium through the stratum corneum to a very high extent, surprisingly, even in the absence of additional permeation enhancers.

The compositions of the invention comprise diclofenac sodium, i.e. 2-[(2,6-dichloro-phenyl)amino]benzeneacetic acid, (mono) sodium salt, in a concentration of about 1 to about 5 wt. % (e.g., from about 1.2 to about 5 wt. %), especially from about 1.2 to about 4 wt. %; e.g., from about 2 to about 4 wt. %, and in particular, 2 wt. %.

Accordingly, the present invention meets the objectives described by providing higher strength emulgel and gel compositions of diclofenac sodium having favorable drug dissolution, viscosity and permeation properties.

Advantageously, compositions of 2% diclofenac sodium according to the invention, when topically administered according to a twice daily (b.i.d) dosage regimen, exhibit a comparable pharmacokinetic profile, with similar systemic exposure to diclofenac, as compared to DSG 1% applied four times daily (q.i.d.).

The compositions afford an important convenience and benefit to U.S. patients and consumers in providing stronger (i.e. >1%) topical diclofenac sodium products that are therapeutically effective even when administered according to a reduced dosing schedule relative to the currently available 1% product.

By "therapeutically effective" is meant effectiveness in the local symptomatic relief of pain and/or inflammation.

DETAILED DESCRIPTION OF THE INVENTION

The ternary solvent systems investigated by the inventors comprise (1) as the volatile water-miscible organic solvent: a lower alcohol selected from $C_2$-$C_4$-alkanols and mixtures thereof, (2) as the non-volatile water-miscible organic solvent: a glycol selected from the group consisting of propylene glycol and polyethylene glycol (200-20000), and mixtures thereof, and (3) water, in specific proportions.

Figure 1:
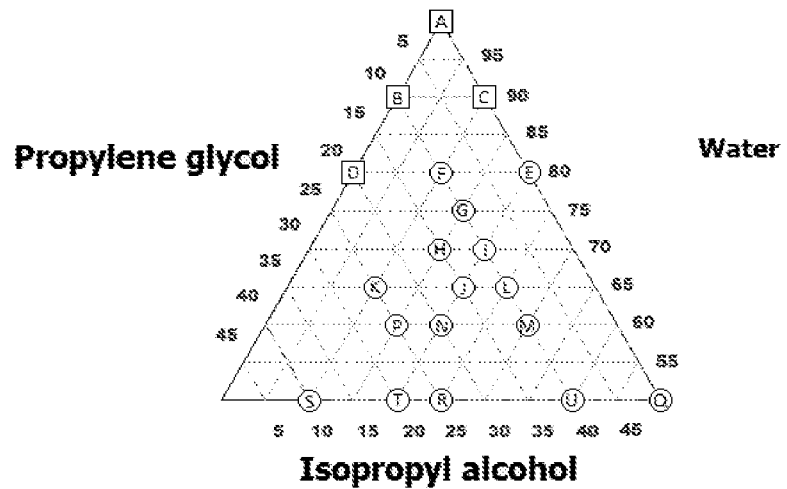
FIG. 1 is a ternary diagram of the solubility of diclofenac sodium, 2 wt %, at 25° C., as determined by UV absorbance, in solvent mixtures comprising isopropyl alcohol (bottom axis), propylene glycol (left axis), and water (right axis) in varying amounts. The data points represent solvent mixtures which are found to be at or above (circles), or below (squares), the target (i.e. 2%) solubility.

FIG. 1 illustrates solubility studies of such solvent systems comprising 2% diclofenac sodium in isopropyl alcohol (IPA), propylene glycol (PG) and water. Complete solubility of the salt, as confirmed by UV absorbance, is achieved across a relatively broad selection of solvent systems, represented by circles in FIG. 1. (Incomplete solubilization is represented by squares.)

Figure 2:
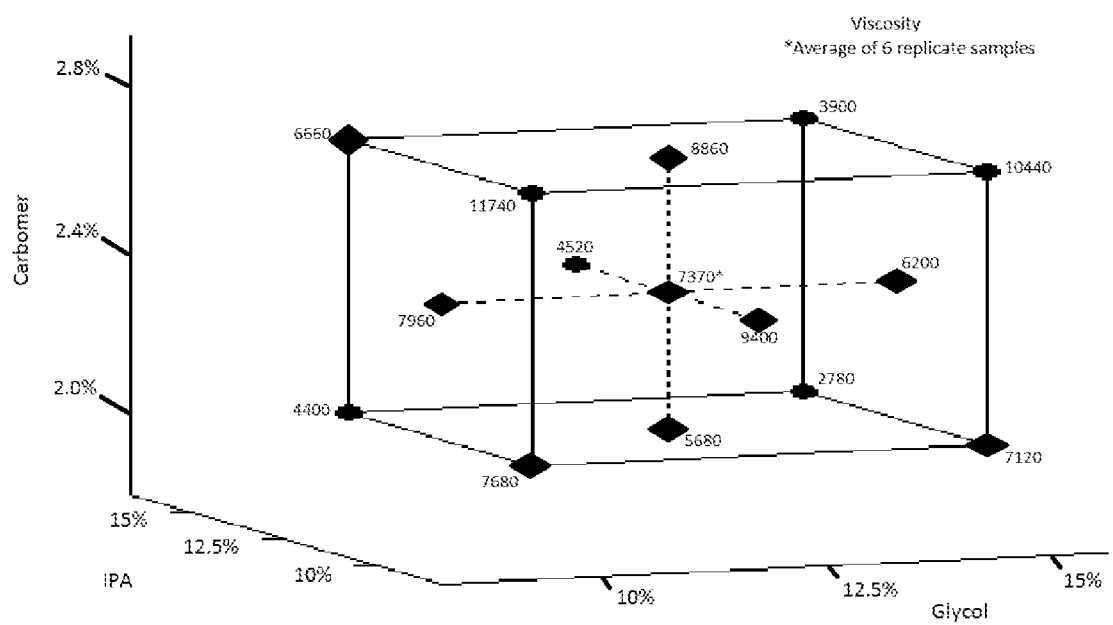
FIG. 2 is a diagram of the viscosities of various solvent mixtures of propylene glycol (x-axis), isopropyl alcohol (z-axis), and carbomer Type C (Carbopol® 980) (y-axis), at 25° C. The data points indicate viscosity within (diamonds), or outside (circles), the target viscosity range of 5,000-10,000 centipoise (cPs).

However, in viscosity studies of the solvent systems represented by circles, to which carbomer Type C (Carbopol® 980) is added at a concentration of 2.0, 2.4 or 2.8%, it has been found that only certain systems provide compositions having the desired viscosity in the range of from about 5,000 to about 10,000 cPs, and optimally in the range of from about 7,000 to about 8,000 cPs, e.g., 7,500 cPs, as shown in FIG. 2 and on Table 1:

TABLE 1

| Sample | Carbomer (wt. %) | Isopropyl alcohol (IPA) (wt. %) | Propylene glycol (PG) (wt. %) | Viscosity (cPs)* |
|---|---|---|---|---|
| E, K, N, R, X | 2.4 | 12.5 | 12.5 | 7370** |
| F | 2.8 | 12.5 | 12.5 | 8860 |
| G | 2.4 | 10 | 12.5 | 9400 |
| H | 2.0 | 15 | 15 | 2780 |
| J | 2.0 | 10 | 15 | 7120 |
| L | 2.0 | 10 | 10 | 7680 |
| M | 2.8 | 10 | 10 | 11740 |
| P | 2.0 | 12.5 | 12.5 | 5680 |

TABLE 1-continued

| Sample | Carbomer (wt. %) | Isopropyl alcohol (IPA) (wt. %) | Propylene glycol (PG) (wt. %) | Viscosity (cPs)* |
|---|---|---|---|---|
| Q | 2.4 | 15 | 12.5 | 4520 |
| S | 2.0 | 15 | 10 | 4400 |
| T | 2.4 | 12.5 | 10 | 7960 |
| W | 2.8 | 15 | 10 | 6660 |

*viscosity (cPs) determined using a Brookfield viscometer fitted with T-bar spindle
**average of 6 values (including A)

As shown above, at carbomer concentration of 2.4%, close to optimal viscosity is achieved with a solvent system comprising: 12.5% IPA/12.5% PG/and the remainder (75%), water (Samples E,K,N,R, X; viscosity of ~7370 cPs); or 12.5% IPA/10% PG/77.5% water (Sample T; 7960 cPs). At a carbomer concentration of 2.0%, viscosity within the preferred range is achieved with a solvent system comprising: 10% IPA/10% PG and the remainder (80%) water (Sample L; 7680 cPs); or 10% IPA/15% PG with 75% water (Sample J; 7120 cPs). At a carbomer concentration of 2.8%, acceptable viscosity is seen with a solvent system comprising: 15% IPA/10% PG/75% water (Sample W; 6660 cPs); or 12.5% IPA/12.5% PG/75% water (Sample F; 8860 cPs).

Based on the above studies, the inventors identified certain novel diclofenac sodium compositions, in the form of emulgels and gels, which comprise the following ingredients ("Formula I"):
(a) 1-5% of diclofenac sodium,
(b) at least about 50% of water,
(c) 5-20% of at least one $C_2$-$C_4$-alkanol,
(d) 5-25% of a glycol solvent selected from the group consisting of propylene glycol and polyethylene glycol (200-20000),
(e) 0.2-5% of at least one gelling agent selected from the group consisting of carbomers, mixtures of carbomers, and mixtures of one or more carbomers with one or more hydroxy- and/or carboxy-substituted celluloses,
(f) 0-10% of a lipid forming an oil phase,
(g) 0-5% of at least one non-ionic surfactant, and
(h) a basic agent to adjust the pH of the total composition to 6-9, all percentages being by weight (w/w) based on the total composition.

In particular, the above compositions of Formula I are subject to the following Preferences (A) and/or (B) and/or (C):
(A)—the respective amounts of lower alcohol (or mixture thereof) and glycol solvent (or mixture thereof), are preferably adjusted to be in a ratio, on a weight-to-weight basis, which is in the range of:
from about 1.5 (alcohol): 1 (glycol) to about 1 (alcohol): 2.5 (glycol);
preferably from about 1.5 (alcohol): 1 (glycol) to about 1 (alcohol): 2.0 (glycol);
further preferably from about 1 (alcohol): 1 (glycol) to about 1 (alcohol): 1.75 (glycol);
e.g., from about 1 (alcohol):1 (glycol) to about 1 (alcohol):1.5 (glycol),
e.g., about 1:1 (wt/wt); and/or
(B)—the lower alcohol and glycol solvent preferably collectively comprise at least about 20%, but preferably not greater than about 40%, and more preferably not greater than about 30%, and even more preferably not greater than about 25%, by weight, of the composition of the invention; and/or
(C)—the glycol solvent and water together preferably comprise at least about 60% by weight of the composition of the invention.

For example, in a preferred embodiment of the compositions of the invention, the gelling agent (e.g., carbomer) concentration is in a range of about 2.0 to about 2.8% (e.g., 2.4%); the glycol solvent concentration is about 10 to about 15% (e.g., 12.5%); the alcohol concentration is about 10 to about 15% (e.g., 12.5%), and water concentration is about 60 to about 70%.

It shall be understood that all percentages recited herein refer to weight percentages (wt/wt based on the total composition) unless otherwise specified.

Accordingly, samples E, K, N, R, X; T; L; J; W and F of Table 1 illustrate preferred embodiments of gelled solvent systems that may be used for preparation of the emulgel or gel compositions of the invention.

Gel compositions of the invention may comprise compositions of Formula I which are essentially free (e.g., having 0%) of component (f) (lipid forming oil phase), and preferably which are essentially free (e.g., having 0%) of each of (f) and (g) (non-ionic surfactant).

Emulsion gel compositions of the invention may comprise compositions of Formula I, wherein (f) and (g) are as follows:
(f) 2-8% of at least one lipid forming the oil phase of the emulsion gel, and
(g) 1-5% of at least one non-ionic surfactant.

The compositions of the invention are clearly different from those exemplified by Asche et al., U.S. Pat. No. 4,917,886, and Caillet-Bois et al., US 2010/0286268, both incorporated by reference, which comprise 2.5×, 3× or even greater amount of isopropyl alcohol as propylene glycol, on a weight-to-weight basis. See also Steiger, US 2010/0234462, incorporated by reference.

Surprisingly, it has been found that compositions of the invention having satisfactory skin permeability can be prepared without added penetration enhancers such as saturated or unsaturated $C_{10}$-$C_{18}$ fatty alcohols (e.g., oleyl alcohol, stearyl alcohol, myristyl alcohol or lauryl alcohol), or hyaluronic acid or its salts, or dimethylsulfoxide (DMSO). Thus, in a preferred embodiment the compositions of the invention are free of any one or more of the foregoing.

Combinations of diclofenac with one or more other active pharmaceutical agents are within the scope of the invention. However, in a further embodiment of the invention, said composition is devoid of any other active pharmaceutical agent (e.g., antifungal drug; e.g., devoid of terbinafine or topically acceptable salts thereof).

The manufacture of the compositions of the invention is effected in a manner known per se, as illustrated in Example 1.

Advantageously, the invention provides compositions comprising 1-5% (w/w), e.g., 1.2-5% (w/w) or 1.2-4% (w/w) or 2-4%, especially 2% (w/w), of diclofenac sodium salt, wherein said compositions (A) have a high skin permeation, (B) show only very low systemic absorption, (C) show essentially no irritation on human skin after administration, (D) are chemically and physically stable when stored at 25° C. and a relative humidity of 60% for 12 months; and (E) can provide long-lasting pain relief.

Thus, the topical pharmaceutical preparations of the present invention exhibit various beneficial properties, as further outlined below.

(A) Having sufficient skin permeation means, e.g., in vitro cumulative permeation on human skin that is, in the case of a 2% diclofenac sodium product, at least about twice that of the marketed product, DSG 1%, at 24 hours.

(B) Very low systemic absorption: Although having high percutaneous absorption, the topical compositions of the invention show only a very low systemic absorption, which means an AUC value (area under curve from t=0 to T=12 h) of less than 30 μg× hour/mL—preferably less than 25, more preferably less than 20, and especially less than 15 μg× hour/mL—derived from a pharmacokinetic graph of "diclofenac concentration (in the blood) versus time" after one application of 2 g thereof to a body area of 400 cm$^2$; "body area" preferably meaning the knee but numeric values indicated are likewise valid for other body areas, e.g. ankle or elbow.

Systemic exposure to diclofenac from the diclofenac sodium emulgel 2% (hereinafter, "DSG 2%" unless otherwise indicated) compositions of the invention (4 g b.i.d. applied on lower extremity joints; 2 g b.i.d. applied on upper extremity joints, up to 2 joints at one time) can be shown to be similar to that of DSG 1% (4 g q.i.d. applied on lower extremity joints; 2 g q.i.d. applied on upper extremity joints, up to 2 joints at one time) and substantially lower than from an oral dose regimen of 50 mg diclofenac sodium tablet administered 3× day (t.i.d.), which is the recommended therapy for treating the signs and symptoms of osteoarthritis.

(C) Essentially no irritation on human skin after administration: The cutaneous tolerance upon intended use in humans is very good.

This can be demonstrated, e.g., in a challenging in vivo test on rabbits which receive a daily 4 hour administration of the product over 28 days; or a photoirritation and/or photosensitization study in guinea pigs. Local tolerability may be assessed in humans by, e.g., phototoxicity, irritation and sensitization; and/or photosensitization studies.

(D) Chemical and physical stability: The compositions are chemically and physically stable, which means having a shelf life of at least 12 months, preferably at least 24 months, when stored at 25° C. and at a relative humidity (r.h.) of 60%. During this time, they maintain full dissolution of the diclofenac sodium salt. Likewise, they are stable for at least 6 months when stored at 40° C. and at a relative humidity of 75%.

By "full dissolution of diclofenac sodium salt" is meant that the active substance is kept fully dissolved (in the emulsion-gel or gel structure of the composition), so that even upon microscopic examination essentially no crystals of diclofenac sodium salt can be observed therein.

Chemical and physical stability further means that (i) that the emulsion-gel structure of the composition is maintained without breaking of the emulsion or loss of elasticity (i.e. slump) and (ii) that the original color of the composition does not visibly change, e.g. via yellowing, over a period of at least 12 months when stored at 25° C. and at a relative humidity of 60%.

Following 6-months storage at 40° C. and relative humidity of 75%, an emulsion gel composition of the invention shows (1) negligible formation of droplets exceeding 30 microns in diameter (i.e. 3 or less; and preferably 2 or less, and most typically 1 or 0, such droplets per 11 mm$^2$ viewing area, as determined by visual microscopy); and (2) low droplet size, i.e. not exceeding 5 microns, in at least 95 wt. %, e.g., at least 98 wt. %, and more typically at least 99 wt. % (e.g., 100 wt. %) of the composition.

(F) Long-lasting pain relief: The 2% diclofenac sodium compositions of the invention can provide more sustained pain relief than other commercially available topical diclofenac sodium preparations such as DSG 1%.

The invention also relates to a method of treating pain or inflammation which comprises topically administering to a mammal, especially a human, in need thereof a therapeutically effective amount of a topical pharmaceutical composition according to the invention.

"Human" includes adults and all children, or, for example, in specific cases may refer, for example, to adults of 18 years of age and older; or children 17 years of age and younger; or adults and children aged 12 years and older.

In one aspect, the invention provides a method for relieving chronic pain and associated inflammation in a patient in need thereof. In another aspect, the invention provides a method for relieving acute pain and associated inflammation in a patient in need thereof.

Thus the invention provides a method for the relief of the chronic pain of osteoarthritis of joints amenable to topical treatment, such as the knees and those of the hands, or the pain of backache.

The invention also provides a method for treating a mammalian subject in need thereof to provide temporary relief from mild-to-moderate aches and pains of muscles and joints such as associated with conditions selected from one or more of arthritis, strains, sprains, bruises and simple backache, by administering to the subject a composition according to the invention.

The invention is also directed to a composition described herein for use in therapy. In particular, this invention provides a composition for use in therapy for the treatment of pain and/or inflammation in a mammalian (e.g., human) subject in need thereof.

In one aspect, the invention provides a composition for use in therapy for relieving chronic pain and associated inflammation in a patient in need thereof. In another aspect the invention provides a composition for use in therapy for relieving acute pain and associated inflammation.

Thus the invention provides a composition for use in therapy for relieving the chronic pain of osteoarthritis of joints amenable to topical treatment, such as the knees and those of the hands, or the pain of backache, in a patient in need thereof.

The invention also provides a composition for use in therapy for treating a mammalian subject in need thereof to provide temporary relief from mild-to-moderate aches and pains of muscles and joints such as associated with conditions selected from one or more of arthritis, strains, sprains, bruises and simple backache.

In other aspects, the compositions may be topically applied for relief of pain, inflammation, and swelling in post-traumatic inflammation of tendons, ligaments, muscles and joints (e.g., due to sprains, strains or bruises), localized forms of soft-tissue rheumatism (e.g., tendonitis, epicondylitis, shoulder-hand syndrome and periarthropathy), and the local management of degenerative joint conditions (e.g., osteoarthritis of the peripheral joints and of the vertebral column).

By "acute pain" is generally meant pain that begins suddenly and is usually sharp in quality. Acute pain may be caused by strains, sprains, and bruises, including blunt, traumatic soft tissue injury and contusions of the limbs, or injury to the joint involving the soft tissue, such as ankle sprain, as well as delayed onset muscle soreness.

Muscle contusions, in particular, are among the most common sports-related injuries (Best, T. M. (1997) *Clin Sports Med;* 16(3): 419-434; Nozaki et al. (2008) *Am J Sports Med;* 36(12): 2354-2362), second only to strains. Contusions are caused by blunt trauma to the outer aspect of the muscle, resulting in tissue and cellular damage and bruising deep within the muscles and between the muscle planes. Fresh impact injuries/contusions usually resolve spontaneously, but may nevertheless cause considerable discomfort, marked functional limitation, absence from work and withdrawal from activities. The goal of treatment is to minimize hemorrhage and inflammation and control pain. Prior to the invention, oral NSAIDs have commonly been used to reduce pain and inflammation in order to facilitate rehabilitation and achieve earlier recovery.

Chronic pain persists despite the fact that an injury has healed. Pain signals remain active in the nervous system for weeks, months, or years. Chronic pain may have originated with an initial trauma/injury or infection, or there may be an ongoing cause of pain, or may occur in the absence of past injury or evidence of body damage. Common chronic pain complaints also include pain from arthritis (osteoarthritis and rheumatoid), and lower back pain (e.g., "simple" backache).

Acute pain may be mild and transient, or may be severe and last for weeks or months. In most cases, acute pain does not last longer than six months and it disappears when the underlying cause of pain has been treated or has healed. Unrelieved acute pain, however, may lead to chronic pain. In general, "acute pain" refers to pain of duration from about 3 to about 6 months from onset; but has also been employed to refer to pain lasting up to about 12 months from onset. Alternatively, the term, "acute pain" has been limited to pain lasting for up to about 30 days from onset, and "chronic pain" to pain lasting six months or greater, with "subacute pain" being pain that lasts up to about six months. Still another definition of "chronic pain," has no fixed duration, but rather refers to pain that extends beyond the expected period of healing.

The topical compositions of the invention are administered by local application to the skin of the pain-affected area to relieve acute and/or chronic pain conditions.

Therapeutically effective doses and dosing regimens may vary according to the type and severity of the condition, as will be understood by the worker in the art.

In the clinical setting, a therapeutically effective dose and dose regimen for the treatment of osteoarthritis of the knee can be demonstrated in a randomized, double-blind, multi-center placebo-controlled study, in which pain is assessed by patients using the WOMAC (Western Ontario and McMaster Universities Osteoarthritis Index) Pain Subindex; and for the treatment of osteoarthritis of the hand can be demonstrated in a randomized, double-blind, multicenter, placebo-controlled study in which pain in the target hand is assessed by the patients on a 100 mm visual analog scale (VAS).

Similarly, a therapeutically effective dose and dose regimen for the treatment of mild-to-moderate aches and pains of muscles and joints can be demonstrated in a randomized, double-blind, multi-center, placebo-controlled study in an acute ankle sprain model showing as a primary outcome statistically significant decreases in pain-on-movement (POM), e.g., of ≥50 mm, on a 100 mm VAS.

When treatment is initiated within three hours of injury, preferably the patient's pain on movement (POM) can be reduced by ≥50% at 24 hours after initiating treatment, as measured by 100 mm Visual Analogue Scale ("VAS") with anchors at 0="No pain" and 100="Extreme pain".

Preferably, statistically significant difference (p≤0.05) in the severity of acute pain can be experienced by the patient as early as one or at most two hours after initial dosing; and meaningful pain relief can be attained only 4 hours after initial dosing.

The compositions can be prescribed by a medical professional such as a doctor or pharmacist. In one aspect, the compositions may be administered by prescription only (RX). In another aspect, the compositions may be administered without a doctor's prescription by a pharmacist ("behind the counter").

Alternatively, the compositions can provide an effective and safe "over-the-counter" (OTC) regimen for the self-treatment of acute as well as chronic pain by a consumer in need thereof. The term "consumer" as used herein shall refer to a mammalian (e.g., human) subject, preferably an adult human that is age 18 years or older, but also including a child 17 years of age or younger. The OTC regimen can omit the steps of consulting with a physician, obtaining a prescription from the physician, and presenting the prescription to a licensed pharmacy in order to obtain the product. This is a significant advantage in affording consumers earlier access to treatment, and thus faster access to pain relief. An OTC treatment regimen addresses a critical need for fast-acting pain relievers in the treatment of the types of injuries most commonly experienced by users of over-the-counter medications, such as strains, sprains, and contusion.

The topical pharmaceutical compositions according to the invention are administered in a manner known per se. Topical administration will generally include any exposed position on the body where it may be advantageous to administer a composition of the invention.

Typically, the compositions of the invention will would be applied locally to affected areas in an amount of approximately 5 to 10 or 15 µL/cm², but generally not higher than about 20 µL/cm².

In one embodiment, the area of application may be about 200-300 cm² (e.g., encompassing both sides of the ankle joint), up to about 400 cm² (extended to an area up to the lower calf and out to the mid-section of the foot), depending on the size of the patient.

Thus, for example, two grams of the composition applied to a body surface of 200/400 cm² delivers 5-10 µL/cm² of the composition (comprising 0.2-0.1 mg/cm² of diclofenac sodium).

In general, a suitable unit dose of DSG2% topical emulsion gel according to the invention for relieving pain of the upper body ("UB") is about 2 grams (e.g., 2 grams, corresponding to 2 mg API); and a suitable unit dose for relieving pain of the lower body ("LB") is about 4 grams (e.g., 4 grams, corresponding to 4 mg API).

By "unit dose" is meant the amount of drug product (or alternatively, the API) that is administered per application.

The compositions may be administered as needed, whether four times daily ("q.i.d."), three times daily ("t.i.d"), or as preferred, two times daily ("b.d." or "b.i.d") (e.g., every 10-12, or 8-12, hours).

In the case of DSG 2% compositions of the invention, a suitable dosing regimen for relief of the pain of osteoarthritis of joints amenable to topical treatment, such as the knees and those of the hands, may comprise b.i.d. topical application of a dosage amount of 2 grams of composition to the pain-affected area of the upper extremities, and/or b.i.d. application of a dosage amount of 4 grams to the pain-affected area of the lower extremities. In one aspect, the total daily dose to any one affected joint of the upper extremities does not exceed 4 grams. In another aspect, the total daily dose to any one affected joint of the lower extremities does not exceed 8 grams. In a further aspect, the total dose does not exceed 16 grams per day over all affected joints.

Alternatively, the DSG 2% compositions of the invention may be topically administered for the temporary relief of mild to moderate aches and pains of muscles and joints associated with, e.g., arthritis, strains, sprains, bruises, and simple backache, by b.i.d. topical application of a dosage amount of 2 grams of composition to the pain-affected area of the body above the waist, i.e. the UB (e.g. hand, elbow, wrist, arm, upper back, etc.) and/or b.i.d. application of a dosage amount of 4 grams to the pain-affected area of the body below the waist, i.e. the LB (e.g. foot, knee, ankle, leg, lower back, etc.). The regimen is repeated for a sufficient number of days (e.g., 7 days) until an effective amount of drug has been administered, but typically for no longer a treatment period than 10 days.

Preferably, the compositions are applied every 8 to 12 hours to one, or concurrently at most two, body sites, not to exceed 2 applications in 24 hours.

By "concurrently" is meant essentially at the same time (e.g., within an interval of 30-60 minutes, and preferably within 15 minutes or less.

Administration of the composition for its therapeutic benefits may be illustrated as follows:

(A) A unit dose administered to the UB, either directed to one site of injury or concomitantly to two sites of injury on the UB (e.g., two 2 g doses, one to each affected area);

(B) A unit dose administered to the LB, either directed to one site of injury or administered concomitantly to two sites of injury on the LB (e.g., two 4 g doses, one to each affected area);

(C) A unit dose administered to the UB and a unit dose to the LB concomitantly administered (e.g., one 2 g dose for UB and one 4 g dose for LB).

Suitable dosing regimens for a DSG 2% composition according to the invention may comprise:

(AA) b.i.d. dosing of 2 grams to the UB and/or 4 grams to the LB, provided that the total combined daily dose to UB and LB does not exceed 16 grams; OR (BB) b.i.d. dosing of 4 grams to one affected area in the LB and/or 4 grams to a second affected area in the LB, provided that the total combined daily dose does not exceed 16 grams.

For each of (AA) and (BB), the b.i.d. regimen is repeated for a sufficient number of days until an effective amount of drug product (or API) has been administered to provide relief from pain and/or inflammation, but preferably for no longer a treatment period than 10 days.

Advantageously, the DSG 2% compositions of the invention, when topically administered b.i.d., can provide a comparable pharmacokinetic profile, with similar systemic exposure of the patient to diclofenac, as that of the same dosage amount of DSG 1% administered q.i.d.

It will be appreciated that the invention also contemplates a kit comprising the drug product in its primary packaging (e.g., tube) and instructions for use, as well as optionally a pre-calibrated dosing device that provides at least one, and preferably two, dosing areas corresponding to one (and preferably two) unit doses of the drug product. For example, the dosing device may include two printed, preferably elongated (e.g., rectangular), drug dosing areas that correspond, respectively, to a unit dose, e.g., 2 or 3 g, for UB treatment and, e.g., 3 or 4 g, for LB treatment. Preferably, the device is adapted to be used as a hand-held applicator, e.g., a dosing sheet or card.

The primary package may be any type of suitable container, but is preferably a tube, e.g. a stock aluminum tube. For examples, tube sizes suitable for consumer use may be 20 g, 50 g or 100 g.

In one embodiment, the first and second dosing areas are distinct and separate, i.e. are non-contiguous (not touching or sharing a common boundary). In an example of such an embodiment, the first and second dosing areas are arranged one above the other, preferably in parallel.

It will be recognized that the elongated dosing area in combination with the opening of the pharmaceutical product tube produces the desired volume (i.e., unit dose) of product. The product substantially fills the dosing area in both the length-wise and width-wise directions.

Suitable hand-held applicators are disclosed in U.S. Patent Publication No. 2010/0100060 (Turner), which is hereby incorporated by reference.

The topical pharmaceutical compositions of the present invention, whether in the form of gels or emulgels, comprise the components (b), (c), (d), (e), (f), (g), (h) and (i) as specified for the various embodiments below.

Water (b) is present in an amount of at least about 50%, preferably from about 55 to about 85%, more preferably from about 55 to about up to 80%, e.g., from about 60 to about 70%, especially from about 60 to about 65%, of the composition of the invention.

Preferred as $C_2$-$C_4$-alkanols (c) are selected from ethanol, isopropanol, and mixtures thereof; and in particular, isopropanol (especially, isopropyl alcohol, 99% by volume). (c) is present in an amount of from about 5 to about 20%, preferably from about 7 to about 15%, especially from about 10 to about 15%, e.g., 12.5%, of the composition of the invention.

Preferably, the glycol solvent (d) is propylene glycol (1,2-propanediol). Alternatively, polyethylene glycol (200-20000), e.g. polyethylene glycol (200-1000), may also be employed as (d). The glycol solvent (d) is present in an amount of from about 5 to about 25%, preferably from about 10 to about 15%, e.g., 12.5%, of the composition of the invention.

Preferably (c) and (d) together comprise no greater than about 40%, preferably from about 20% to about 40%, and more preferably from about 20 to about 30%, even more preferably from about 20 to about 25%, of the composition of the invention.

In preferred embodiments, the compositions of the invention are essentially free of any additional water-miscible hydrocarbon co-solvents of diclofenac beyond the required (c) alcohol and (d) glycol solvent. For example, the compositions may be free of Transcutol® (i.e. diethylene glycol monoethyl ether).

Carbomers (e), in the context of the present invention, are defined as homo- or copolymers of acrylic acid. Carbopol® is the trade name for a general class of high molecular weight homo and co-polymers of acrylic acid crosslinked with a polyalkenyl polyether, commercially available from Lubrizol Advanced Materials, Inc. (Ohio, USA). Carbopol® homopolymers are polymers of acrylic acid that are cross-linked, e.g. with an allyl ether of pentaerythritol (allyl pentaerythritol) or an allyl ether of sucrose (allyl sucrose). Carbopol® copolymers are polymers of acrylic acid formed, e.g., with minor levels of long chain (i.e. $C_{10}$-$C_{30}$) alkyl acrylate co-monomers, crosslinked with allyl pentaerythritol. Homopolymers are generally preferred in the compositions of the invention.

Especially preferred are carbomers 980, 940, 981, 941, 974, 934 and 910. Particularly preferred are Carbopol® 980 (Carbomer Homopolymer Type C), having viscosity of 40,000-60,000 cP, and Carbopol® 974 (Carbomer Homopolymer Type B), having viscosity of 29,400-39,400 cP—especially Carbopol® 980—, and analogous carbomer products from other suppliers. Carbopol® type polymers are flocculated powders of particles averaging about 0.2 micron in diameter. The flocculated powders average 2 to 7 microns as determined by Coulter Counter. Also useful are: Carbopol® Ultrez 10 polymer (Carbomer Interpolymer Type A), a cross-linked polyacrylic acid polymer) having viscosity of 45,000-65,000 cP; and Carbopol Ultrez 20 polymer (acrylates/$C_{10-30}$ alkyl acrylate crosspolymer). (Viscosity, 47,000-67,000 cP, being taken at 0.5 wt. % at pH 6; see Lubrizol Pharmaceutical Bulletin 1, Edition: May 31, 2011).

Various hydroxy- or carboxy-substituted celluloses can be combined with the carbomer to increase viscosity. Examples include hydroxy-substituted celluloses such as hydroxypropylcellulose (HPC); hydroxypropyl methylcellulose (HPMC); hydroxyethylcellulose (HEC); and carboxy-substituted celluloses such as carboxymethylcellulose (CMC). The hydroxycellulose may be included in the composition in a range of from about 0.1 to about 1%. Mixed gellants comprising combinations of carbomer with HEC or HPC have been found to provide higher viscosity compositions, however at the expense, in some instances, of yield value ("yield value" being the ability of the gel to maintain its shape upon dispensing, i.e. without slumping, as determined by visual inspection 5 minutes following application to a surface). Accordingly, in certain embodiments of the invention, it is preferred that the gellant comprise one or more carbomers in the absence of a hydroxylated or carboxylated cellulose.

As a further component of the compositions, Pemulen® polymeric emulsifiers of Lubrizol, which are high molecular weight, cross-linked copolymers of acrylic acid and a hydrophobic comonomer, may optionally stabilize oil-in-water emulsions at typical use levels of 0.15 to 0.4%.

The carbomer, carbomer mixture or carbomer/cellulose mixture (e) is utilized in an amount of about 0.2 to about 5%, preferably from about 1 to about 4%, more preferably from about 2 to about 3%, e.g., about 2.4% or 2.8%, based on the composition of the invention. The compositions of the invention preferably have viscosities of no more than 10,000 cPs, preferably from about 5,000 to about 10,000 cPs, e.g., from about 5,000 to about 9,000 cPs, optimally 7,000-8,000 cPs, as determined with a Brookfield viscometer fitted with T-bar spindle.

The liquid lipid (f) forms the oily phase of the emulsion-gel compositions of the invention. It can be of a vegetable or animal nature, or partly or completely synthetic. There come into consideration lipids without ester linkages, e.g., hydrocarbons, and lipids having ester linkages, e.g., glycerides—i.e. fatty acid esters of glycerol—, especially triglycerides, or esters of fatty acids, e.g., with $C_1$-$C_{36}$-alkanols, especially $C_8$-$C_{36}$-alkanols. Examples of suitable hydrocarbons are, e.g., mineral oil, paraffin or petroleum jelly. Suitable glycerides are, e.g., olive oil, castor oil, or sesame oil, it being possible for all said oils also to be hydrogenated; caprylic/capric acid triglyceride or glycerol mono-, di- and tri-esters with palmitic and/or stearic acid. Esters of fatty acids with $C_1$-$C_{36}$-alkanols are, e.g., beeswax, carnauba wax, cetyl palmitate, lanolin, isopropyl myristate, isopropyl stearate, oleic acid decyl ester, ethyl oleate, or $C_6$-$C_{12}$-alkanoic acid esters—especially caprylic/capric acid esters—with saturated fatty alcohols, especially $C_{12}$-$C_{18}$ saturated fatty alcohols.

Preferably, the liquid lipid (f) comprises $C_6$-$C_{12}$-alkanoic acid $C_{12}$-$C_{18}$-alkyl esters. Particularly preferred is a mixture of liquid paraffin and $C_6C_{12}$-alkanoic acid $C_{12}$-$C_{18}$-alkyl esters—especially caprylic/capric acid esters with $C_{12}$-$C_{18}$ saturated fatty alcohols (coco-caprylate/caprate, e.g. Cetiol® (BASF)).

The liquid lipid(s) (f) are present in a total amount of from 0 to about 10%, and in the emulgel compositions of the invention are preferably present in an amount of from about 2 to about 8%, preferably from about 4 to about 6%. If a mixture of paraffin and coco-caprylate/caprate is used, the amount of each of the paraffin and the coco-caprylate/caprate is preferably from about 1.5 to about 3%, especially from about 2 to about 3.0%, and most preferably from about 2.25 to about 2.75%, of the total composition. The gel compositions of the invention are preferably essentially free of the lipid component (e.g., (f) is 0%).

(g) A non-ionic surfactant may also be employed in the compositions of the invention. Examples include esters of fatty acids, especially a $C_8$-$C_{18}$ fatty acid, with monohydroxy or, preferably, polyhydroxy compounds, e.g. ethylene glycol, glycerol, anhydrosorbitol or pentaerythritol. Another important group of non-ionic surfactants is represented by the poly(oxyethylated) surfactants, which mean compounds that have at least one active hydrogen, e.g., fatty alcohols—especially a $C_8$-$C_{18}$ fatty alcohol—, fatty acids—especially a $C_8$-$C_{18}$ fatty acid—, sorbitan fatty acid esters, $C_1$-$C_{18}$-alkylphenols or $C_8$-$C_{18}$-alkylamines, and that all are poly (oxyethylated), preferably with from 2 up to 40 ethylene glycol or ethylene oxide units.

Examples of the above mentioned non-ionic surfactants are partial glycerin fatty acid esters, such as glycerin monostearate; partial fatty acid esters of sorbitan or polyoxyethylene sorbitan, such as sorbitan monolaurate or polyethylene glycol (5 to 20) sorbitan monostearate or monooleate; polyoxyethylene (3 to 40) fatty alcohol ethers, such as polyoxyethylene (3 to 12) lauryl ethers or polyoxyethylene (5 to 40) cetostearyl ethers; polyoxyethylene fatty acid esters, such as polyoxyethylene (8 to 100) stearate; polyoxyethylene $C_4$-$C_{12}$-alkylphenyl ethers, e.g. polyoxyethylene (nonyl or octyl)phenyl ethers; or polyoxyethylene $C_8$-$C_{18}$-alkylamines, e.g. polyoxyethylene oleylamine. Preferred are polyoxyethylene (10 to 30) fatty alcohol ethers, in particular polyoxyethylene (20) cetostearyl ether (e.g. Cetomacrogol 1000).

The non-ionic surfactant (g) may be present in an amount of from 0 to about 5%, preferably from about 0 to about 3%, e.g., from about 1.5 to about 2.5%, of the total emulgel composition. The gel compositions may be essentially free of this component (e.g, (g) is 0%).

The basic agent (h) used to neutralize the carbomer and adjust the pH of the total composition to 6-9—especially 7-9, e.g., 7-8—is preferably ammonia. For example, strong ammonia (e.g., 29%) can be employed in an amount of from about 0.5 to about 2.5%, especially from about 1.5 to about 2.25%, of the total composition, depending on the carbomer. Alternatively, dilute, i.e. 10%, ammonia solution, can be utilized in appropriate amounts, for example about 1.25 to about 10% of the total composition, depending on the carbomer. In general, (h) can be present e.g. in amount of from about 0.1 to about 10% of the total composition.

To the extent water is introduced by the basic agent (h) (e.g., 10% ammonia solution), or other component, the water shall be counted toward the weight percent requirement of component (b) ("water") of the compositions of the invention.

The compositions of the inventions may optionally include further routine excipients known in the art, for example fragrances/perfumes (e.g., *eucalyptus*), antioxidants, e.g. butylhydroxytoluene, antimicrobial preservatives, e.g. benzyl alcohol, benzalkonium chloride or parabens ($C_1$-$C_7$-alkyl esters of 4-hydroxybenzoic acid, e.g. methyl 4-hydroxybenzoate), and/or coloring agents.

Penetration enhancers such as, e.g, saturated or unsaturated $C_{10}$-$C_{18}$ fatty alcohols selected from the group consisting of stearyl alcohol, myristyl alcohol, lauryl alcohol and oleyl alcohol, may optionally be included in the emulsion gel or gel compositions. If included, suitable amounts would be from about 0.5% to about 2.5%. However, the compositions of the invention are preferably free of such permeation enhancers, which can affect the stability of the composition.

A preferred embodiment of the topical pharmaceutical compositions of the invention comprises the following ("Formula II"):
(a) 2% of diclofenac sodium salt,
(b) at least about 55% of water,
(c) 10-20% of at least one $C_2$-$C_4$-alkanol,
(d) 10-20% of at least one glycol solvent selected from the group consisting of 1,2-propanediol and polyethylene glycol (200-20000),
(e) 0.5-5% of at least one gelling agent selected from the group consisting of carbomers,
(f) 0-10% of a lipid forming an oil phase,
(g) 0-5% of at least one non-ionic surfactant, and
(h) a basic agent to adjust the pH of the total composition to 6-9.

A preferred embodiment of the invention in the form of an emulsion gel comprises compositions of Formula II wherein (f) and (g) comprise:
(f) 3-7% of at least one liquid lipid forming the oily phase of the emulsion-gel, and
(g) 1-3% of at least one non-ionic surfactant.

A preferred embodiment of the invention in the form of a gel comprises compositions of Formula II which are essentially free of component (f) (lipid forming oil phase), and preferably which are essentially free of (f) and (g) (non-ionic surfactant).

An even more preferred embodiment of the topical pharmaceutical compositions of the invention, in the form of an emulgel, comprises ("Formula III"):
(a) 2% (w/w) of diclofenac sodium salt,
(b) at least about 60% of water,
(c) 10-15% of at least one $C_2$-$C_4$-alkanol,
(d) 10-15% of at least one glycol solvent selected from the group consisting of 1,2-propanediol and polyethylene glycol (200-20000),
(e) 0.7-3% of at least one gelling agent selected from the group consisting of carbomers, and
(f) 3-7% of at least one liquid lipid forming the oily phase of the emulsion-gel,
(g) 1-3% of at least one non-ionic surfactant, and
(h) 0.5-3% of a base to adjust the pH of the total composition to 6.5-8.5.

Similar to the compositions of Formula I, the compositions of Formulas II and III are subject to the previously stated Preferences (A), (B) and/or (C).

A further example of a composition of the invention in the form of an emulgel comprises:
(a) 2% (w/w) of diclofenac sodium salt,
(b) at least about 60% of water,
(c) from about 10 to about 15% of isopropanol,
(d) from about 10 to about 15% of propylene glycol,
(e) from about 0.7 to about 3% of carbomer or mixtures thereof, preferably Carbomer homopolymer, type C
(f) from about 3 to about 7% of at least one liquid lipid forming the oily phase of the emulsion-gel selected from mineral oil and cocoyl caprylocaprate, and mixtures thereof,
(g) from about 1 to about 3% of polyoxyl 20 cetostearyl ether, and
(h) a basic agent to adjust the pH of the total composition to 7-9.

The emulgel compositions of the invention in their preferred aspect may be described as opaque, white, soft, homogenous, cream-like oil-in-water topical emulsions.

The topical pharmaceutical compositions according to the invention are administered in a manner known per se to the affected portions of the skin.

While the compositions preferably consist of the sodium salt of diclofenac as the active pharmaceutical ingredient, other useful diclofenac salts include metal salts, such as alkali metal or alkaline earth metal salts, for example potassium, magnesium or calcium salts, aluminum salts or transition metal salts, such as zinc or copper salts, or corresponding salts with ammonia or organic amines such as diethylamine.

The concentration of the diclofenac in the composition is preferably 2% (based on the sodium salt), but may include other concentrations as well (e.g., 0.1-10%).

The materials, methods and examples herein are illustrative only and are not intended to be limitative of the invention.

Example 1

Several 2% diclofenac sodium compositions of the invention are prepared as shown on the following Table 2.

TABLE 2

| Ingredient | Function and element of claims | Formulation No. and amount of ingredient (g/100 g) | | | | | | |
|---|---|---|---|---|---|---|---|---|
| | | 38 | 39 | 40 | 41 | 42 | 43 | 44 |
| Active ingredient | | | | | | | | |
| Diclofenac sodium | Active Ingredient (a) | 2.0 | 2.0 | 2.0 | 2.0 | 2.0 | 2.0 | 2.0 |
| Other ingredients | | | | | | | | |
| Isopropyl alcohol | Solvent (c) | 12.5 | 12.5 | 10 | 10 | 10 | 12.5 | 12.5 |
| Propylene glycol | Solvent (d) | 12.5 | 12.5 | 10 | 10 | 15 | 12.5 | 12.5 |
| Cocoyl caprylocaprate | Liquid lipid (f) | 2.5 | 2.5 | 2.5 | 2.5 | 2.5 | 2.5 | 0 |
| Mineral oil | Liquid lipid (f) | 2.5 | 2.5 | 2.5 | 2.5 | 2.5 | 2.5 | 0 |
| Polyoxyl 20 cetostearyl ether | Non-ionic surfactant (g) | 2.0 | 2.0 | 2.0 | 2.0 | 2.0 | 2.0 | 0 |

TABLE 2-continued

| Ingredient | Function and element of claims | Formulation No. and amount of ingredient (g/100 g) | | | | | | |
|---|---|---|---|---|---|---|---|---|
| | | 38 | 39 | 40 | 41 | 42 | 43 | 44 |
| Carbomer homopolymer, type C Lubrizol Carbopol 980 | Gelling agent (e) | 2.4 | 2.4 | 0 | 2.0 | 2.8 | 0 | 2.4 |
| Carbomer interpolymer, type A Lubrizol Carbopol Ultrez 10 | Gelling agent (e) | 0 | 0 | 1.8 | 0 | 0 | 2.2 | 0 |
| Strong Ammonia | Neutralizing agent for carbomer (h) | 2.16 | 1.94 | 1.47 | 1.67 | 2.26 | 1.53 | 1.80 |
| Perfume | Fragrance | 0.1 | 0.1 | 0.1 | 0.1 | 0.1 | 0.1 | 0.1 |
| Water, purified | Diluent, solvent | qs | qs | qs | qs | qs | qs | qs |
| pH (7-8) unless otherwise indicated | | ~9 | | | | | | |

In the process for manufacture of the above formulations: (a) is dissolved in (d) and part of (c). Said solution is added to a mixture prepared by dispersing (e) in the remainder of (b) and (c) which is neutralized by adding (i). All remaining components—(f), (g) (which are included in all of the formulations except No. 44), and optional ingredients such as BHT and/or perfumes, if present—are heated and slowly added to the former mixture. Upon mixing a homogeneous emulsion-gel (or gel) is obtained.

Example 2—Stability

The stability of a composition of the invention can be tested via an assay of diclofenac sodium. In doing so, the formulation is stored under various conditions (temperature/relative humidity) and for various storage times, e.g., at 25° C./60% r.h.; 30° C./75% r.h.; and 40° C./75% r.h., for 3, 6 and 12 months, after which the amount of diclofenac sodium is determined.

It is thus demonstrated that the active substance is stable even under demanding storage conditions for long periods of time.

Example 3—Microscopic Examination

Formulation No. 39, an oil-in-water emulsion gel, is examined under 100× times magnification and scrutinized for the presence of any crystals of diclofenac sodium salt. No crystals of diclofenac sodium salt are observed.

Example 4—In Vitro Cumulative Permeation

Full-thickness human skin samples from aesthethic surgery, kept frozen at −80° C. until use, are partly thawed and dermatomed to 0.6 mm, then mounted horizontally, dermis side down, on vertical static Franz cells with 1.75 cm$^2$ administration area at 37° C. The receptor phase in the cell (approximately 8 ml), comprising phosphate buffered saline, 7.4, is mixed with a magnetic stirrer.

20 mg/cm$^2$ of each of Formulation Nos. 39 and 44, as well as of VEG 2%, DSG 1% and VEG 1% as references, is applied on skin samples pre-tested for similar tritiated water permeation.

Punches are applied under non-occlusive conditions. At various time intervals, i.e. 0, 2, 4, 8, and 24 h, 1 ml samples of the receptor phase are collected. The removed receptor volume is replenished with fresh receptor solution after each withdrawal. The amount of diclofenac permeating the skin is determined by HPLC analysis of the collected fractions after filtration.

Figure 3:
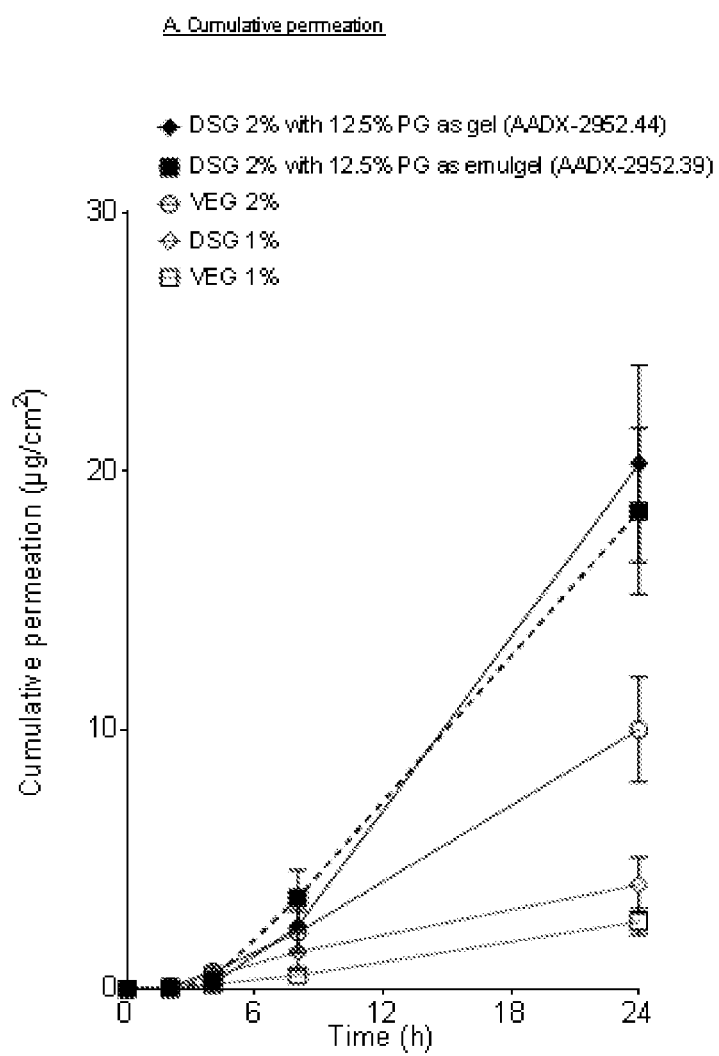
FIG. 3 and FIG. 4 are graphs of the cumulative permeation ($\mu g/cm2$) (FIG. 3) and flux ($\mu g/cm2/hr$) (FIG. 4) taken over a period of 24 hours (hrs) of an emulgel having formulation 39 of Table 1 below (referred to as "DSG 2% with 12.5% PG as emulgel (AADX-2952.39)") and a gel having formulation 44 of Table 1 (referred to as "DSG 2% with 12.5% PG as gel (AADX-2952.44)"), by comparison to that of VEG 1%, VEG 2% (referred to as Voltaren® Forte), and DSG 1%.
Figure 4:
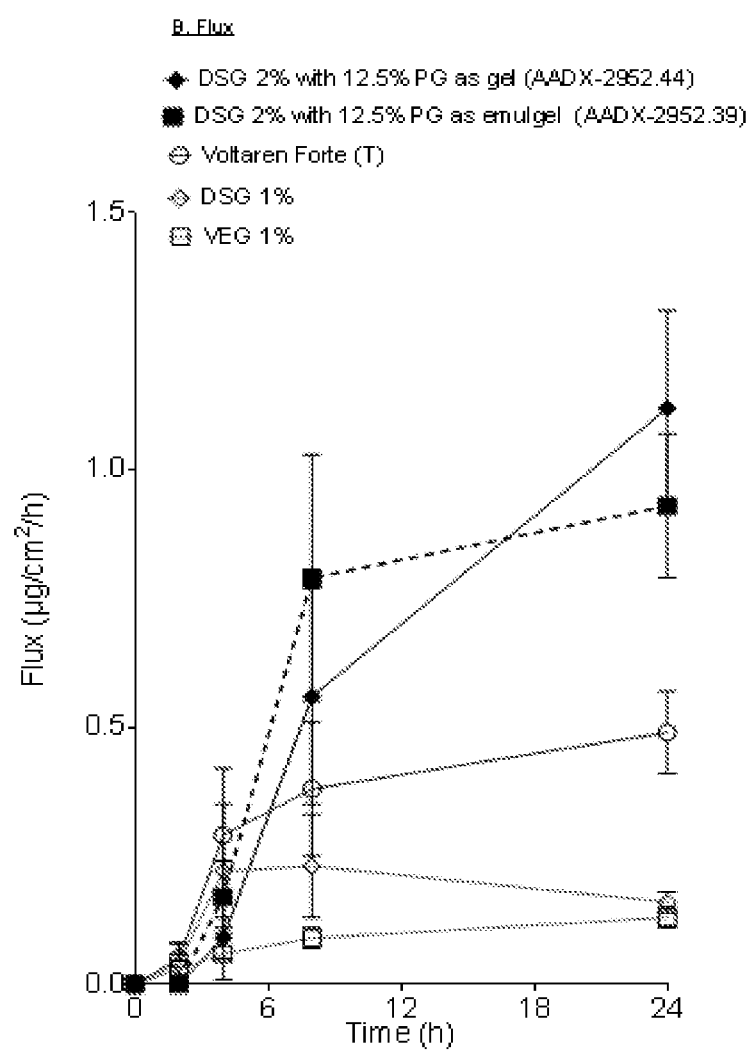

In vitro drug permeation, expressed as cumulative permeation (A) (μg/cm2) and flux (B) (μg/cm2/h), is graphically depicted in FIGS. 3 and 4, respectively. Values represent means±standard error of the mean (s.e.m) of 4-5 replicates (n=4-5). (The test provides relative values in comparison to the reference, although not absolute values.)

As shown in FIG. 3, cumulative permeation of Formulation Nos. 39 and 44 is greater than 2× that of DSG 1% and VEG 1%; as well as being nearly (No. 39) or about (No. 44) 2× that of VEG 2%.

As shown in FIG. 4, flux of the Formulation Nos. 39 and 44 is greater than 2× that of DSG 1% and VEG 1%; as well as being nearly (No. 39) or over (No. 44) 2× that of VEG 2% (referred to in FIG. 4 as "Voltaren Forte (T)").

Example 5—Local Skin Tolerance in Rabbits (N=6)

The local skin tolerance of Formulations 39, 41, 42, 43, 44 of Table 1, using DSG 1% as reference, is investigated in vivo on the same animal by semi-occlusive dermal repeated application over a 4 hour exposure period over each of 28 consecutive days. The test items are applied at the dose of 0.10 mL (the reference, 0.21 mL) on an undamaged zone of 4 cm$^2$, which is equivalent to 25 mg/cm$^2$ (50 mg/cm$^2$ of reference). A control area is untreated.

Clinical cutaneous examinations of the skin (visual examinations) are carried out before the first application and then for 4 weeks just before the new topical application, and 24 hours after the last application. The skin reactions are scored in accordance with the following scoring scale:

| Erythema and Eschar Formation | |
|---|---|
| No erythema | 0 |
| Very slight erythema (barely perceptible) | 1 |
| Well defined erythema | 2 |
| Moderate to severe erythema. | 3 |
| Severe erythema (beef redness) with eschar formation preventing grading of erythema | 4 |

Figure 5:
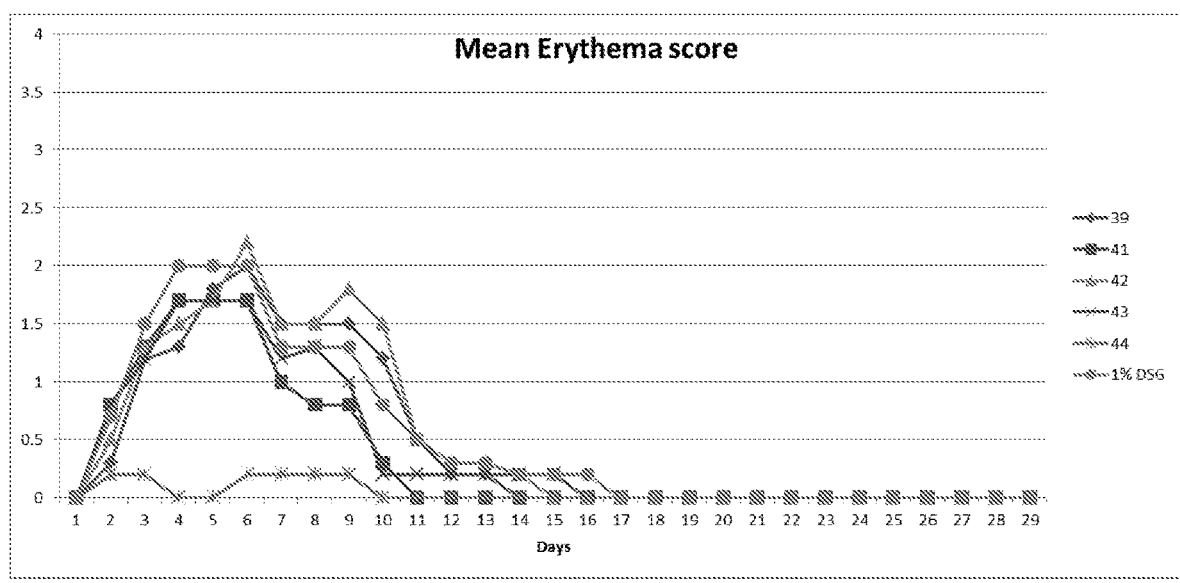
FIG. 5 is a graph of the mean erythema score of several compositions of the invention determined at application (Day "1") and for a period of 28 days thereafter, with DSG 1% as reference.

The cutaneous tolerance of Formulation Nos. 39, 41, 42, 43, 44, is observed to be comparable to or improved relative to the reference, DSG 1%, as demonstrated in FIG. 5.

What is claimed is:

1. A topical pharmaceutical composition in the form of a gel or emulsion gel which comprises:
   (a) 2% of diclofenac sodium salt,
   (b) at least about 55% of water,
   (c) from about 10 to about 15% of isopropyl alcohol, (d) from about 10 to about 15% of 1,2-propanediol,
(e) from about 2 to about 3% of at least one gelling agent selected from the group consisting of carbomers,
(f) from 0 to about 10% of a lipid forming an oil phase,
(g) from 0 to about 5% of at least one non-ionic surfactant, and
(h) a basic agent to adjust the pH of the total composition to 6-9, wherein (c) and (d) together comprise from about 20% to about 25% of the composition, and the viscosity of the composition is from about 5,000 to about 10,000 cPs at 25° C., all percentages being by weight (w/w) based on the total composition.

2. A topical pharmaceutical composition according to claim 1 in the form of an emulsion gel, comprising:
(f) from about 2 to about 8% (w/w) of at least one lipid forming the oil phase of the emulsion gel; and
(g) from about 1 to about 5% (w/w) of at least one non-ionic surfactant.

3. A topical pharmaceutical composition according to claim 2 wherein (f) comprises mineral oil and cocoyl caprylocaprate and (g) is selected from the group consisting of esters of fatty acids with monohydroxy or polyhydroxy compounds, polyoxyethylated surfactants and mixtures thereof.

4. A topical pharmaceutical composition according to claim 1 in the form of a gel, which is free of (f).

5. A topical pharmaceutical composition according to claim 4, which is free of (f) and (g).

6. A topical pharmaceutical composition according to claim 1, in the form of an emulsion gel, which comprises:
(a) 2% (w/w) of diclofenac sodium salt,
(b) at least about 60% of water,
(c) from about 10 to about 15% of isopropyl alcohol,
(d) from about 10 to about 15% of 1,2-propanediol,
(e) from about 2 to about 3% of at least one gelling agent selected from the group consisting of carbomers, and
(f) from about 3 to about 7% of at least one liquid lipid forming the oily phase of the emulsion-gel,
(g) from about 1 to about 3% of at least one non-ionic surfactant, and
(h) a basic agent to adjust the pH of the total composition to 7-9, wherein (c) and (d) together comprise from about 20% to about 25% of the composition, and the viscosity of the composition is from about 5,000 to about 10,000 cPs at 25° C., all percentages being by weight (w/w) based on the total composition.

7. A topical pharmaceutical composition according to claim 6 wherein (f) comprises mineral oil and cocoyl caprylocaprate and (g) is selected from the group consisting of esters of fatty acids with monohydroxy or polyhydroxy compounds, polyoxyethylated surfactants and mixtures thereof.

8. A topical pharmaceutical composition according to claim 6 wherein (g) comprises polyoxyl 20 cetostearyl ether.

9. A topical pharmaceutical composition according to claim 1, said composition having a high skin permeation, (B) said composition showing a very low systemic absorption only, (C) said composition showing essentially no irritation on human skin after administration as demonstrated by a mean erythema score of less than 2.5 on a scale of 0-4, and (D) said composition being chemically and physically stable when stored at 25° C. and a relative humidity of 60% for 12 months, in that (i) the emulsion-gel structure of the composition is maintained without breaking of the emulsion, and (ii) the original color of the composition does not visibly change over a period of at least 12 months when stored at 25° C. and at a relative humidity of 60%, and (E) said composition further keeping the diclofenac sodium salt fully dissolved, which means that even upon microscopic examination at 100× magnification no crystals of diclofenac sodium salt can be observed therein.

10. A method for treating pain or inflammation in a mammalian subject comprising topically administering a therapeutically effective amount of a composition according to claim 1 to a mammalian subject in need thereof.

11. A method according to claim 10 for treating acute pain or inflammation.

12. A method according to claim 10 for treating chronic pain or inflammation.

13. A method for treating a mammalian subject in need thereof to provide temporary relief from mild-to-moderate aches and pains of muscles and joints associated with conditions selected from one or more of arthritis, strains, sprains, bruises and backache, by administering to the subject a therapeutically effective amount of a composition according to claim 1.

14. A kit for administering a composition for the treatment of pain or inflammation comprising
(a) a composition according to claim 1
(b) instructions for topically administering the composition, and optionally
(c) a pre-calibrated dosing device.

15. A topical pharmaceutical composition according to claim 1 in the form of a gel which comprises:
(a) 2% of diclofenac sodium salt,
(b) at least about 55% of water,
(c) from about 10 to about 15% of isopropyl alcohol,
(d) from about 10 to about 15% of 1,2-propanediol,
(e) from about 2 to about 3% of at least one gelling agent selected from the group consisting of carbomers, and
(h) a basic agent to adjust the pH of the total composition to 6-9, wherein (c) and (d) together comprise from about 20% to about 25% of the composition, and the viscosity of the composition is from about 5,000 to about 10,000 cPs at 25° C., said composition being free of (f) and (g), all percentages being by weight (w/w) based on the total composition.

16. A topical pharmaceutical composition according to claim 1 in the form of a gel or emulsion gel which comprises:
(a) 2% of diclofenac sodium salt,
(b) at least about 55% of water,
(c) about 12.5% of isopropyl alcohol,
(d) about 12.5% of 1,2-propanediol
(e) from about 2 to about 3% of at least one gelling agent selected from the group consisting of carbomers,
(f) from 0 to about 10% of a lipid forming an oil phase,
(g) from 0 to about 5% of at least one non-ionic surfactant, and
(h) a basic agent to adjust the pH of the total composition to 6-9, wherein the viscosity of the composition is from about 5,000 to about 10,000 cPs at 25° C., all percentages being by weight (w/w) based on the total composition.

17. A topical pharmaceutical composition in the form of a gel or emulsion gel which consists essentially of:

(a) 2% of diclofenac sodium salt,
(b) at least about 55% of water,
(c) about 12.5% of isopropyl alcohol,
(d) about 12.5% of 1,2-propanediol
(e) from about 2 to about 3% of at least one gelling agent selected from the group consisting of carbomers,
(f) from 0 to about 10% of a lipid forming an oil phase,
(g) from 0 to about 5% of at least one non-ionic surfactant, and
(h) a basic agent to adjust the pH of the total composition to 6-9, wherein the viscosity of the composition is from about 5,000 to about 10,000 cPs at 25° C., all percentages being by weight (w/w) based on the total composition.

18. A topical pharmaceutical composition according to claim 17 in the form of a gel which is free of (f) and (g).

19. A composition according to claim 1 wherein the gelling agent comprises carbomer homopolymer.

20. A composition according to claim 15 wherein the gelling agent comprises carbomer homopolymer.

21. A composition according to claim 16 wherein the gelling agent comprises carbomer homopolymer.

22. A composition according to claim 17 wherein the gelling agent comprises carbomer homopolymer.

23. A composition according to claim 1 which is free of penetration enhancers selected from saturated or unsaturated $C_{10}$-$C_{18}$ fatty alcohols, hyaluronic acid or its salts, and dimethylsulfoxide.

24. A composition according to claim 15 which is free of penetration enhancers selected from saturated or unsaturated $C_{10}$-$C_{18}$ fatty alcohols, hyaluronic acid or its salts, and dimethylsulfoxide.

25. A composition according to claim 16 which is free of penetration enhancers selected from saturated or unsaturated $C_{10}$-$C_{18}$ fatty alcohols, hyaluronic acid or its salts, and dimethylsulfoxide.

26. A composition according to claim 17 which is free of penetration enhancers selected from saturated or unsaturated $C_{10}$-$C_{18}$ fatty alcohols, hyaluronic acid or its salts, and dimethylsulfoxide.

27. A topical pharmaceutical composition in the form of a gel or emulsion gel which consists essentially of:
(a) 2% of diclofenac sodium salt,
(b) at least about 55% of water,
(c) about 12.5% of isopropyl alcohol,
(d) about 12.5% of 1,2-propanediol
(e) from about 2 to about 3% of at least one carbomer homopolymer,
(f) from 0 to about 10% of a lipid forming an oil phase,
(g) from 0 to about 5% of at least one non-ionic surfactant, and
(h) a basic agent to adjust the pH of the total composition to 6-9, all percentages being by weight (w/w) based on the total composition.

28. A method for treating pain or inflammation in a mammalian subject comprising topically administering a therapeutically effective amount of a composition according to claim 6 to a mammalian subject in need thereof.

29. A method for treating pain or inflammation in a mammalian subject comprising topically administering a therapeutically effective amount of a composition according to claim 16 to a mammalian subject in need thereof.

30. A method for treating pain or inflammation in a mammalian subject comprising topically administering a therapeutically effective amount of a composition according to claim 17 to a mammalian subject in need thereof.

31. A method for treating pain or inflammation in a mammalian subject comprising topically administering a therapeutically effective amount of a composition according to claim 27 to a mammalian subject in need thereof.

* * * * *